United States Patent [19]

Pavcnik et al.

[11] Patent Number: 5,397,351
[45] Date of Patent: Mar. 14, 1995

[54] PROSTHETIC VALVE FOR PERCUTANEOUS INSERTION

[76] Inventors: Dusan Pavcnik, Klanec #15, Nova Gorica, Slovenija, 65000, Yugoslavia; Sidney Wallace, 3324 Pittsburg, Houston, Tex. 77005; Kenneth C. Wright, 1802 Haver, Houston, Tex. 77006

[21] Appl. No.: 699,195

[22] Filed: May 13, 1991

[51] Int. Cl.$^6$ ............................ A61F 2/02; A61F 2/24
[52] U.S. Cl. .......................................... 623/11; 623/2; 623/3; 623/1; 623/900
[58] Field of Search ...................... 623/1, 11, 2, 3, 900

[56] References Cited

U.S. PATENT DOCUMENTS

| | | |
|---|---|---|
| 3,130,419 | 4/1964 | Edwards ................................ 623/2 |
| 3,143,742 | 8/1964 | Cromie .................................. 623/2 |
| 3,571,815 | 3/1971 | Somyk . |
| 3,574,865 | 4/1971 | Hamaker . |
| 3,626,518 | 12/1971 | Leibinsohn . |
| 3,911,502 | 10/1975 | Boretos . |
| 4,580,568 | 4/1986 | Gianturco . |
| 4,648,383 | 3/1987 | Angelchik . |

OTHER PUBLICATIONS

Gregorio Rabago, *A Worldwide Overview of Valve Usage*, Chapter 1 of *Heart Valve Replacement: Current Status and Future Trends*, Futura Publishing Company, Inc., Mount Kisko, N.Y. (G. Rabago, D. Cooley ed. 1987) (citing Hufnagel C. A. Harvey W. P. Rabil P. J. Mc- Dermott R. F.: Surgical Correction of Aortic Insufficiency, *Surgery*, 35:673, 1954).

Cary W. Akins, Mortimer J. Buckley, Wm. M. Daggett, W. Gerald Austen, Alan D. Hilgenberg, and Marshall L. Jacobs, *Ten-Year Follow-Up of the Starr-Edwards Prosthesis*, Chapter 10 of *Heart Valve Replacement: Current Status and Future Trends*, Futura Publishing Company, Inc., Mount Kisko, N.Y. (G. Rabago, D. Cooley ed. 1987).

David J. Mehlman, *Radiographic and Cineradiographic Evaluation of Heart Valve Prostheses*, Chapter 11 of *Heart Valve Replacement: Current Status and Future Trends*, Futura Publishing Company, Inc., Mount Kisko, N.Y. (G. Rabago, D. Cooley ed. 1987).

*Primary Examiner*—David Isabella
*Assistant Examiner*—Debra S. Brittingham
*Attorney, Agent, or Firm*—Woodard, Emhardt, Naughton, Moriarty & McNett

[57] ABSTRACT

A prosthetic valve comprises a poppet, a seat and a restraining element. The poppet, seat and restraining element include an insertion form for percutaneously inserting into a fluid passageway within a living body and an operational form for operating within the fluid passageway. The valve is self-expanding so that upon insertion the valve automatically assumes the operational form. In the operational form the poppet is movably restrained between the valve seat and restraining element. The poppet seals against the valve seat to prevent fluid flow through the valve and unseats from the valve seat to permit fluid flow through the valve.

16 Claims, 6 Drawing Sheets

PROSTHETIC VALVE FOR PERCUTANEOUS INSERTION

BACKGROUND OF THE INVENTION

This invention relates to prosthetic valves which might find application as prosthetic aortic valves for percutaneous insertion and placement within a fluid passageway of a living body.

One example of a prosthetic valve is that of an aortic heart valve controlling blood flow from the heart within the human body. Occasionally valve failure will occur as a result of disease, wherein a heart valve becomes incompetent. During the pumping action of the heart, blood either regurgitates or leaks back across the incompetent valve against the normal direction of blood flow. This type of valve failure results in a decrease in heart pumping efficiency, the heart having to work harder to pump the required blood flow. Therefore, prosthetic valves have been developed and are manufactured which replace diseased or incompetent natural valves of the heart.

Replacement of heart valves with prosthetic valves within the human body was perhaps first documented by Hufnagel in 1954. Hufnagel C. A. Harvey W. P. Rabil P. J. McDermott R. F.: Surgical Correction of Aortic Insufficiency, *Surgery*, 35:673, 1954. Since then numerous prosthetic valves have been developed, including both mechanical and biological heart valves. Mechanical heart valves are generally of two designs, either a ball-in-cage valve or a disc valve. One example of a mechanical heart valve is that of Boretos, U.S. Pat. No. 3,911,502, which describes a composite heart valve poppet for use with ball-in-cage artificial heart valves. The poppet includes a core of rigid material covered by an elastomer jacket. Leibinsohn, U.S. Pat. No. 3,626,518, discloses an artificial cardiac valve having characteristics of both a ball valve and a disc valve for improved streamlined blood flow and reduced turbulence. Hamaker, U.S. Pat. No. 3,574,865, discloses a prosthetic sutureless heart valve, the heart valve fastening to the heart via a two-piece snap ring. Somyk, U.S. Pat. No. 3,857,815, discloses a suture ring for a heart valve, wherein a cylindrical collar extends radially from the valve to facilitate attachment.

With regard to currently available prosthetic valves, the physician/patient must weigh the advantages and disadvantages of each type of prosthetic valve. However, no choice currently exists regarding the installation and placement of the prosthetic heart valve. Currently, installation of prosthetic valves requires general anesthesia and open-heart surgery. As a result, the recipient of the prosthetic valve is subjected to the inherent risk of mortality associated with surgery. Therefore, a major factor when deciding whether to replace a valve and choosing the type of prosthetic valve is the mortality risk associated with the surgery. Furthermore, because biological valves have a limited useful life and thrombosis can lead to obstruction of the mechanical valve, repeat surgeries may be required to maintain the valve which further increase the mortality risk to the patient.

A need therefore exists for a prosthetic heart valve which does not require surgery for installation and placement and, therefore, avoids the mortality risk associated with surgery. Such a valve would provide treatment for an incompetent valve and the aortic regurgitation resulting therefrom without requiring general anesthesia and open-heart surgery. Ideally, such a valve would be placed in a fluid passageway via transcatheter techniques, similar to that currently used for the installation and placement of endovascular stents.

SUMMARY OF THE INVENTION

A prosthetic valve for percutaneous insertion and placement within a fluid passageway of a living body according to one embodiment of the present invention includes a valve seat, a restraining element, and a poppet. The valve assembly includes a first insertion form for percutaneous insertion into the passageway. The valve assembly includes a second larger operational form for operation within the passageway, wherein the valve seat has means for sealing against the passageway and an opening for sealing engagement with the poppet and the restraining element has means for restraining passage of the poppet therethrough while permitting fluid flow therethrough. The poppet is movably restrained within the passageway between the valve seat and the restraining element, wherein the poppet seals against the opening in the valve seat to prevent fluid flow therethrough and the poppet unseats from the valve seat to permit fluid flow therethrough.

The invention also involves a method for inserting a deformable prosthetic valve within a fluid passageway of a living body. The method includes the steps of placing a deformable aortic prosthetic valve assembly within a distal end of a first sheath, wherein the valve includes a first insertion form and a second larger operational form and the first sheath encompasses the valve when the valve is in the first smaller insertion form, locating the distal end of the first sheath in the passageway, and placing the valve in the passageway by removing the first sheath from the passageway while holding the valve in place.

One object of the present invention is to provide an improved method and apparatus for a prosthetic heart valve.

Another object of the present invention is to provide a prosthetic heart valve which does not require open-heart surgery and general anesthesia for installation and placement.

Another object of the present invention is to provide a prosthetic heart valve which can be percutaneously inserted and placed within a fluid passageway of a living body.

Related objects and advantages of the present invention will become apparent from the following description.

DESCRIPTION OF THE PREFERRED EMBODIMENT

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1:
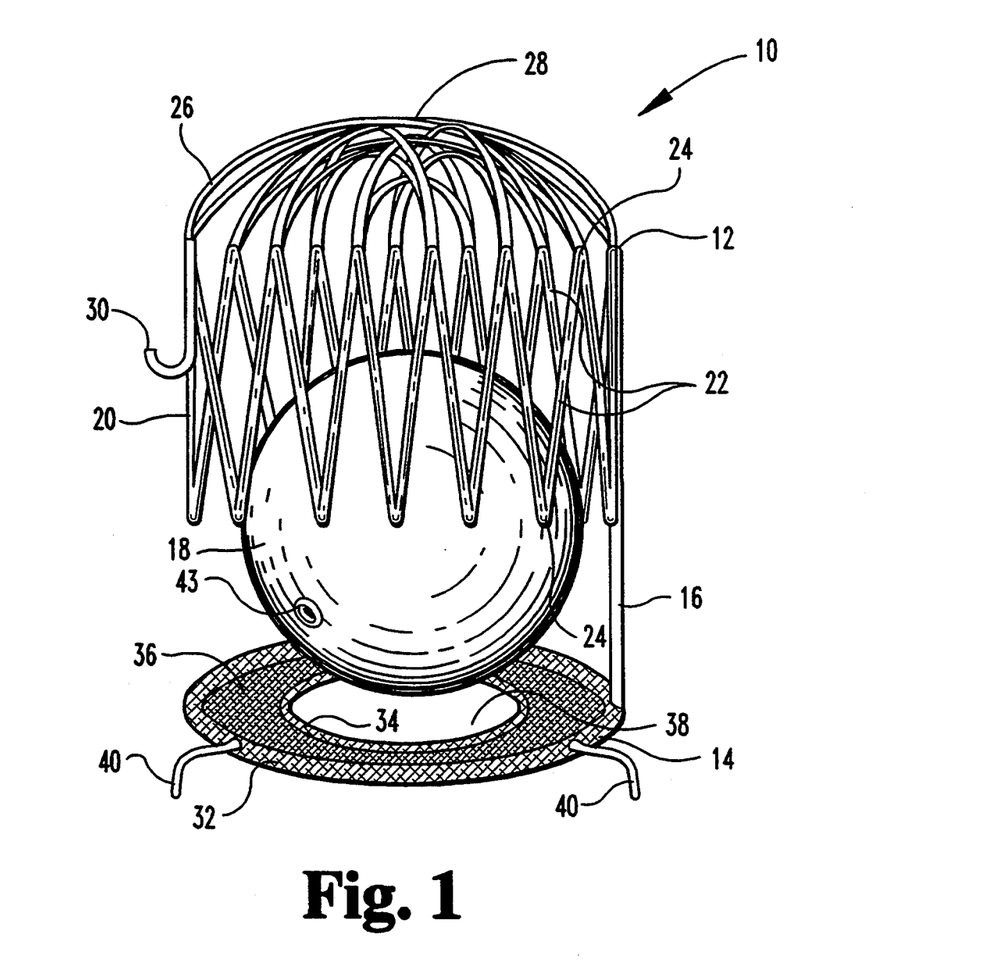
FIG. 1 is a perspective view of a prosthetic valve according to one embodiment of the present invention.

Referring now to FIG. 1, a prosthetic valve 10 is shown in its operational form. Valve 10 includes a smaller insertion form in addition to its operational form, wherein the valve collapses to its smaller form for installation. Valve 10 is a ball-in-cage type valve including a restraining element, comprising a cage 12, attached to a valve seat, comprising a ring 14. Means for fixedly disposing the restraining element relative to the valve seat is provided by a length of stainless steel tubing 16.

Restrained within the valve is a movable poppet comprising a balloon 18. Balloon 18 translates between a sealing position seated against ring 14 and an open position restrained within cage 12. Cage 12 allows fluid to pass therethrough while restraining balloon 18 from migrating when in the open position.

Valve 10 is elastically compressible, wherein cage 12 and ring 14 resiliently compress into their respective smaller installation forms and, upon placement within a fluid passageway, automatically self-expand into their operational forms. In accompanying FIGS. 1-4, valve 10 assumes its smaller shape by cage 12 collapsing radially inward and ring 14 collapsing longitudinally for insertion into a fluid passageway. Tubing 16 is not required to be compressible as its operational form has a sufficiently small cross-section to allow for transcatheter percutaneous installation and placement. Cage 12 includes a self-expanding stent 20 in its construction for supporting the fluid passageway open to allow for travel of balloon 18 therein. Stent 20 comprises a wire formed into a closed zig-zag configuration including an endless series of straight wire sections 22 joined by a plurality of bends 24 to form the stent. Preferably, the stent 20 is a Gianturco self-expanding stent as described in U.S. Pat. No. 4,580,586, which description is incorporated herein by reference.

Attached to bends 24 at one end of stent 20 are four lengths of flat, flexible stainless steel wire 26. Wires 26 loop across stent 20 to form a restraining element 28 of valve 10 for preventing passage of balloon 18 therethrough. The number of wires attached to bends 24 can vary; however, four to six lengths of wire are provided for optimum performance of the valve. Fewer wires may not adequately restrain balloon 18 within valve 10, while greater numbers of wires may promote thrombosis. Soldering provides an effective attachment mechanism of wires 26 to bends 24 of stent 20, with welding and other attachment means known in the art also being contemplated.

Also contemplated is a restraining element 28 formed by a single flexible wire wherein the wire is bent into a zig-zag shape having straight sections and bends. The bends of the single flexible wire attach to stent 20 with the straight sections looping across the end of the stent similar to the lengths of flexible wire 26.

In the preferred embodiment a number of hooks or barbs 30 are attached to cage 12. More than one barb may be provided depending on the size of the filter and the corresponding fluid flow resistance which is reacted by the passageway via the attaching hooks. Because the passageway is typically tissue (although prosthetic passageways are envisioned), the fluid force on the filter is distributed so as not to tear the filter from the tissue causing migration of the valve. Also assisting placement and fixation of the valve is stent 20. Depending on the particular stent design, upon expansion of the cage or stent within the fluid passageway sufficient resilient stress may be stored within the stent to create a combination pressure/friction effect which tends to keep the stent wires 24 in contact with the surrounding tissue. Tissue overgrowth may also occur to prevent migration of the valve.

Ring 14 is comprised of two ring-type springs 32 and 34 covered with a fine mesh 36 preferably formed of a tightly woven nylon or dacron material. Nylon mesh 36 provides effective fluid flow blockage so that flow passes through opening 38 when balloon 18 is unseated. Springs 32 and 34 elastically flex to create a smaller cross-section for ease of insertion. Springs 32 and 34 are preferably formed by attaching the ends of an individual length of stainless steel wire together. A number of barbs 40, similar to barbs 30, are preferably attached at various points around spring 32 for stabilization of the valve following placement of ring 14.

Balloon 18 is preferably a detachable inflatable latex balloon. Balloon 18 is deflated for insertion to provide the smaller form required for transcatheter percutaneous insertion. Once the cage and ring assembly are in place within the fluid passageway, balloon 18 is inserted within the valve between ring 14 and cage 12. Balloon 18 is then filled with a material to prevent deflation of the balloon. Balloon 18 includes a simple one-way valve 43 which allows for inflation via a needle or similar penetrating medium. Once the material has been injected and the needle withdrawn, one-way valve 43 seals the material within the balloon to maintain the balloon's spherical shape. In the preferred embodiment, the material is a silicone rubber which pressurizes the balloon to maintain its spherical shape. Other materials are also contemplated which harden within balloon 18 to maintain its shape.

Figure 2:
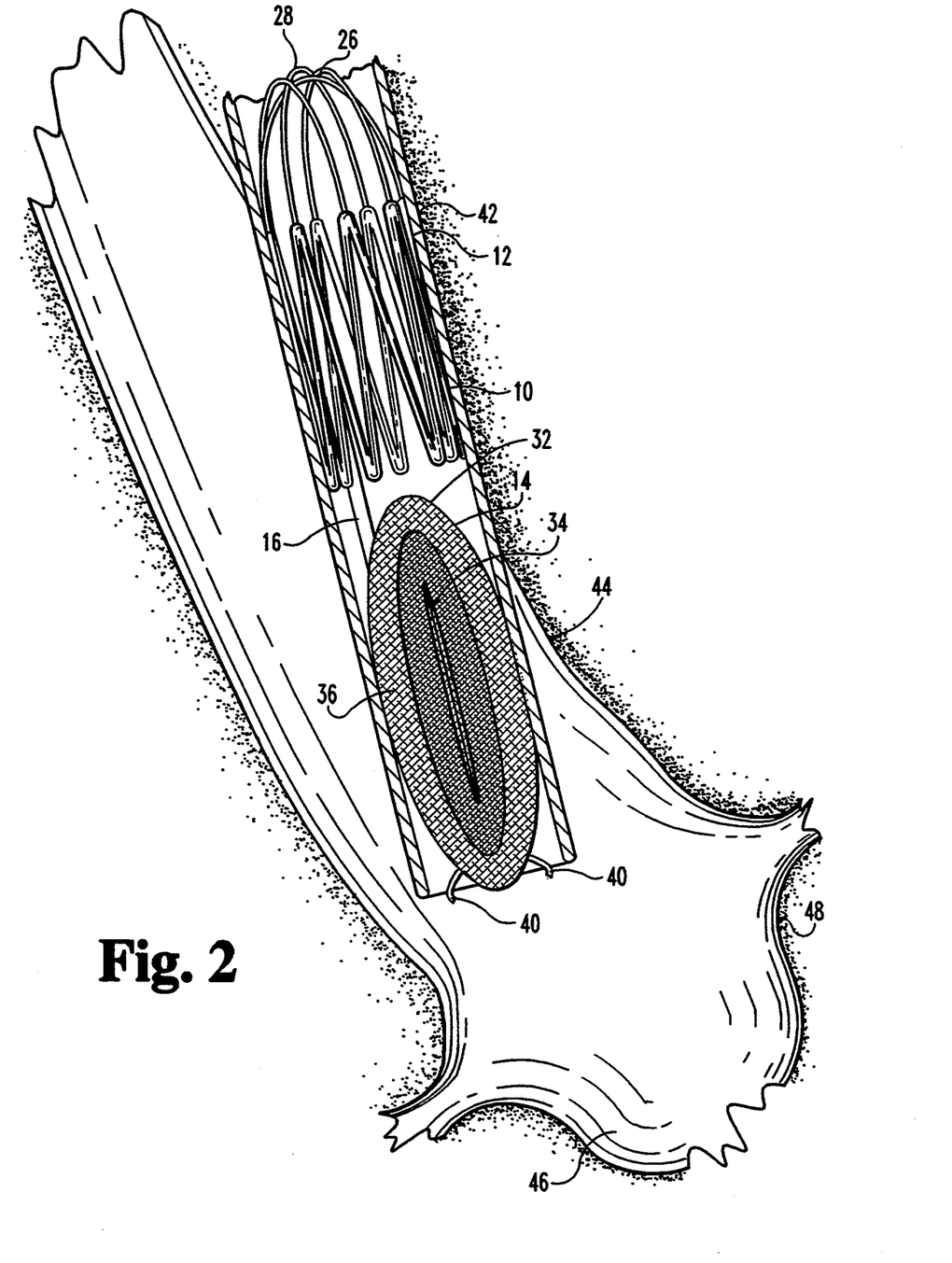
FIG. 2 is a side cross-sectional view of the prosthetic valve of FIG. 1 collapsed within a distal end of a sheath for insertion into a passageway.

Referring to FIG. 2, insertion of the valve 10 begins by collapsing the cage 12 and ring 14 within a sheath 42, such as an 11-12 French Teflon sheath. The sheath is then percutaneously inserted into a fluid passageway and the valve is held in place while the sheath is withdrawn to deploy the valve. Because the valve is self-expanding, it opens as it exits the sheath. Proper positioning of the valve can be verified by known techniques, such as radiography.

Referring again to FIG. 2, valve 10 is depicted in its compressed state constrained within sheath 42. Sheath 42 is shown inserted into fluid passageway or vessel 44 above a ventricle 46 of the heart. Also contemplated is sheath 42 inserted remote from ventricle 46, wherein the sheath is advanced within a fluid passageway to reach ventricle 46; i.e. percutaneous insertion at the groin region. Cage 12 is collapsed radially while ring 14 is collapsed longitudinally or along the longitudinal axis of sheath 42. Tubing 16 maintains the spatial relationship of cage 12 to ring 14 and connects the two so that the cage 12 and ring 14 may be inserted as a unit. Barbs 40 are depicted facing ventricle 46 so that upon release of ring 14, it will attach to aortic walls 48 above the ventricle, thus stabilizing the filter within vessel 44 and preventing migration of the valve during deployment of cage 12. Wire segments 26 deform longitudinally as well to accommodate stent 20 in its collapsed form.

Figure 3:
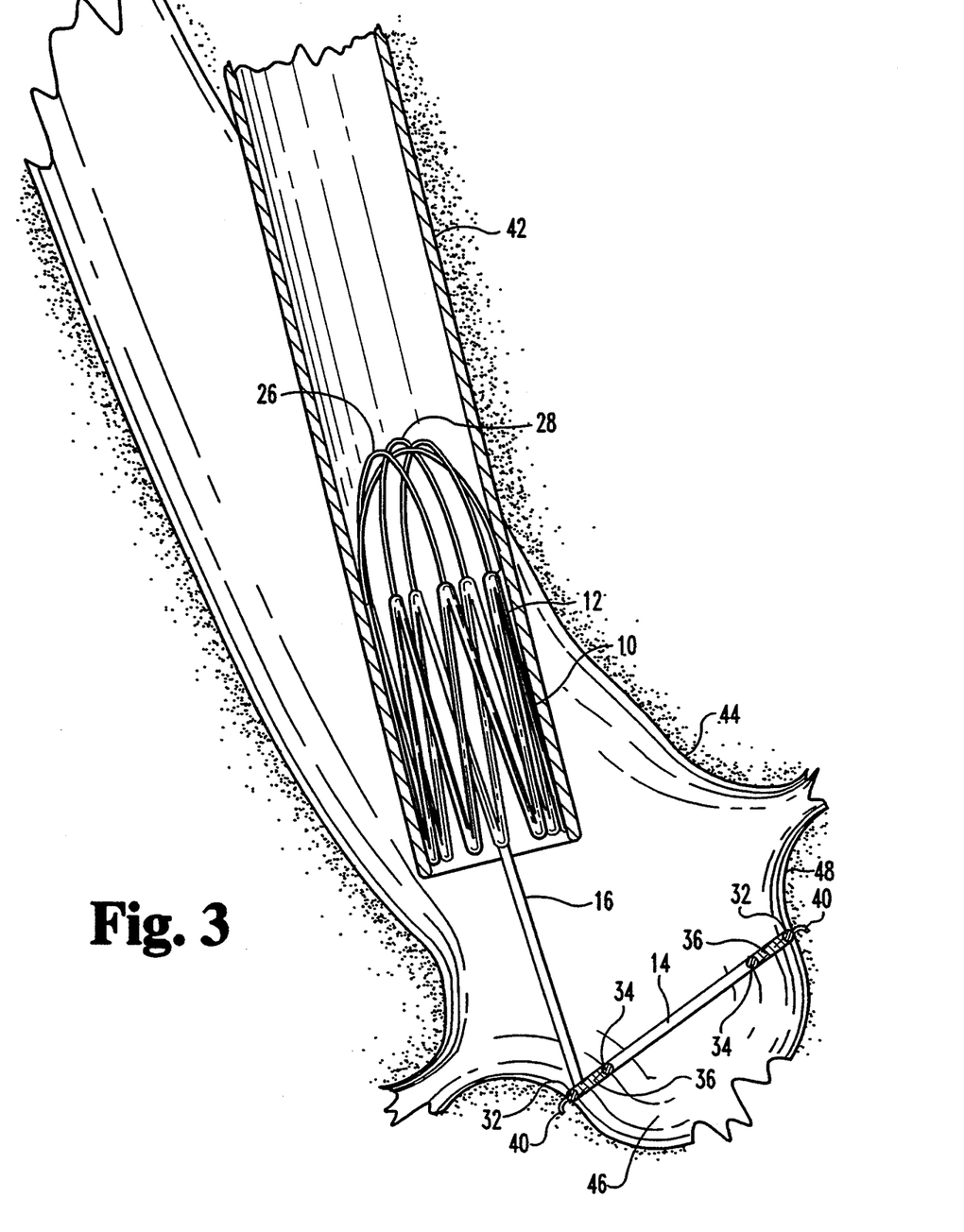
FIG. 3 is a side cross-sectional view of the prosthetic valve of FIG. 1 partially deployed.

Referring now to FIG. 3, ring 14 is depicted in its operational form deployed and attached to aortic wall 48. Barbs 40 attach ring 14 to wall 48 while cage 12 remains compressed within sheath 42. Ring 14 is delivered from sheath 42 using a pusher catheter (not shown) slidable within sheath 42, wherein the pusher catheter holds the valve in correct placement as the sheath is withdrawn. Once ring 14 is deployed, the cage 12 is deployed from sheath 42 to complete placement of valve 10.

Figure 4:
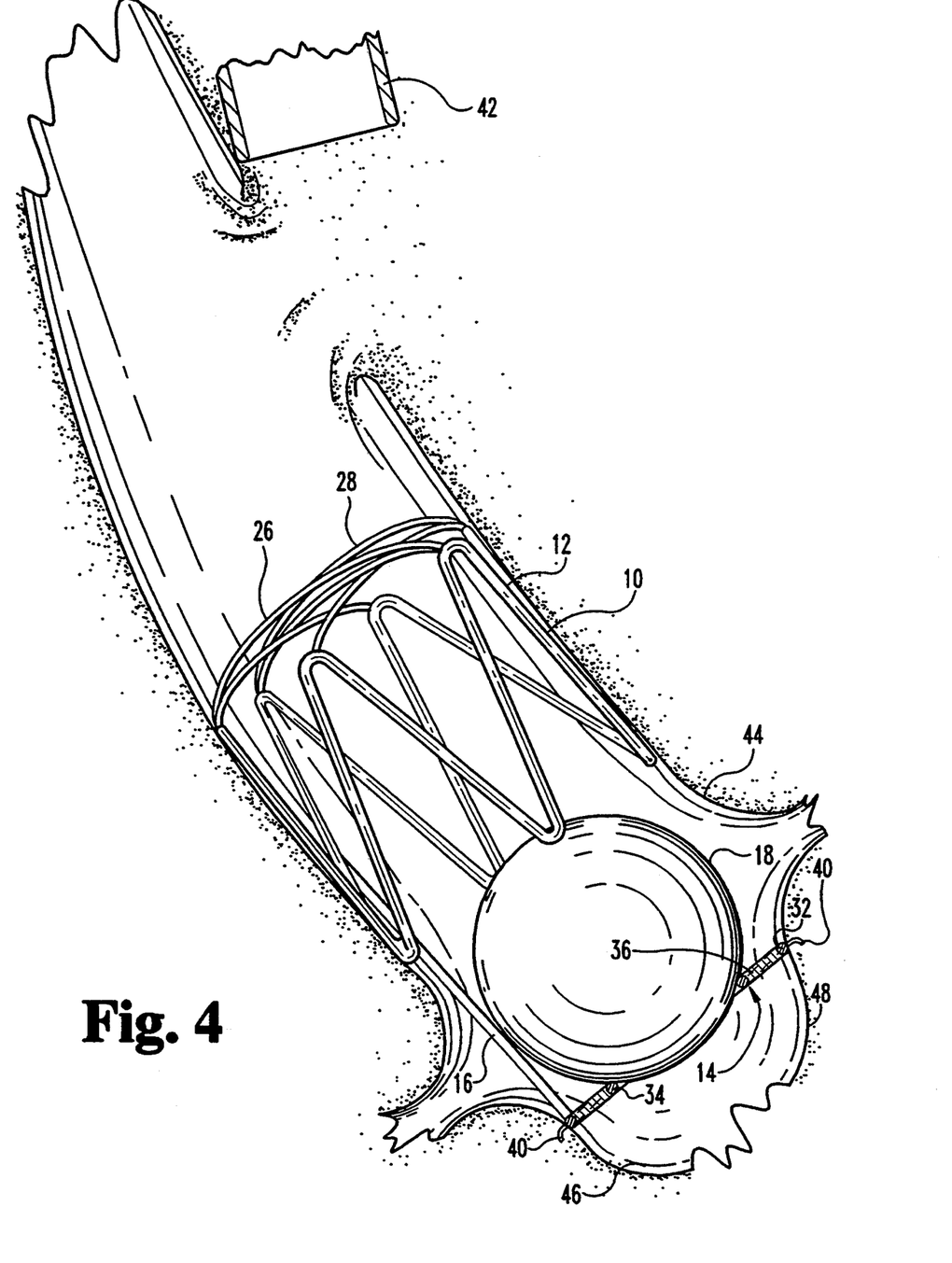
FIG. 4 is a side cross-sectional view of the prosthetic valve of FIG. 1 fully deployed within the passageway.

Referring now to FIG. 4, both cage 12 and ring 14 are shown deployed with tubing 16 connecting the two. However, cage 12 and ring 14 need not be connected to provide an operable prosthetic valve because barbs 30 and stent 20 can fix the cage and barbs 40 can locate ring 14 to maintain the integrity of valve 10 within passageway 44. Tubing 16, however, provides an added measure of safety should either cage 12 or ring 14 loosen from their respective vessels.

Figure 5:
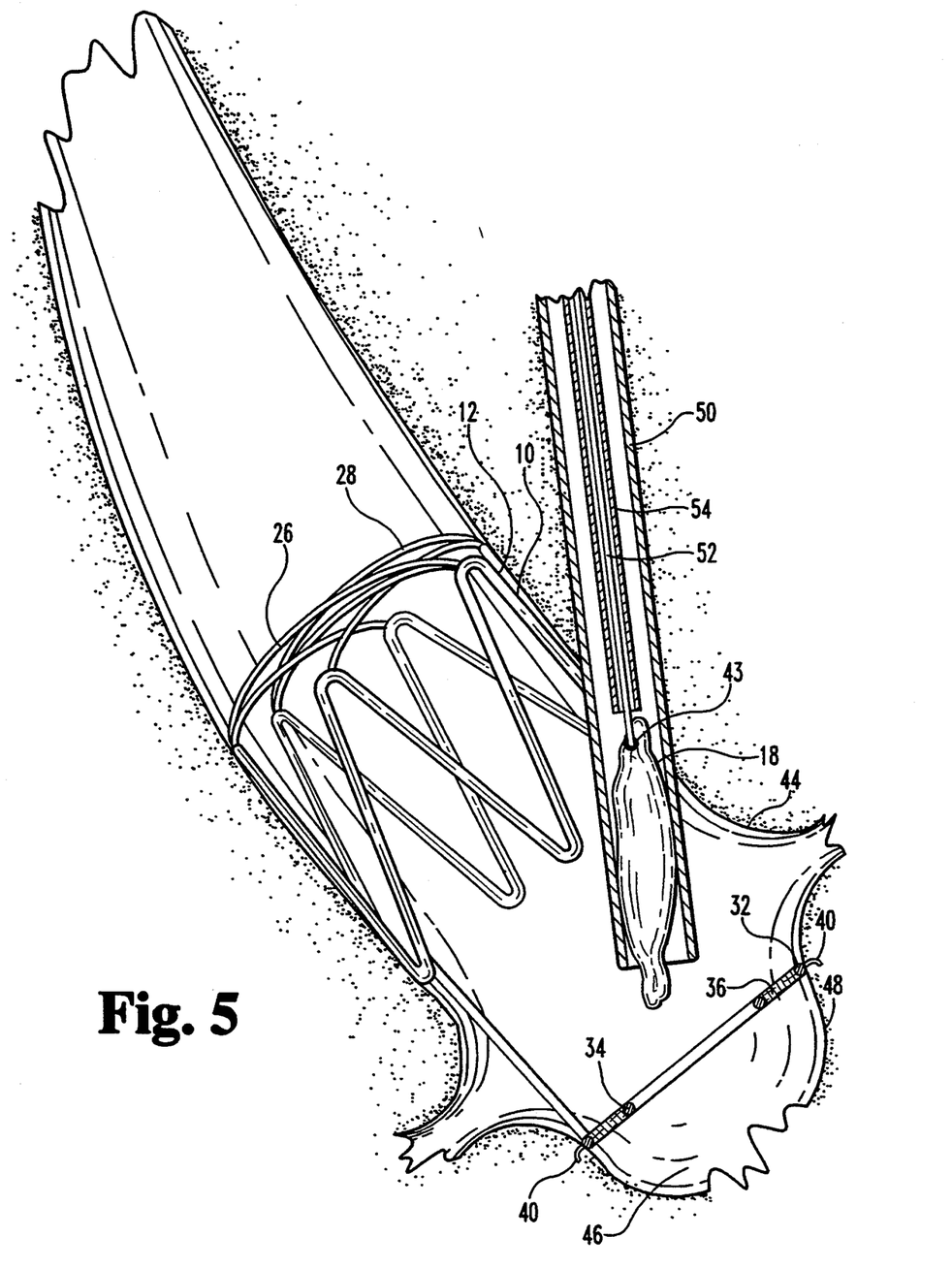
FIG. 5 is a side cross-sectional view of the prosthetic valve of FIG. 1 with a balloon collapsed within a distal end of a sheath for insertion into the passageway.

The next step is deployment of the balloon. Referring to FIG. 5, the balloon 18 is placed at the tip of a narrow gauge catheter 50, such as a 5-French high-flow catheter. Catheter 50 contains tube 52 within pusher sheath 54. The catheter 50 is inserted in the fluid passageway 44 through the cage 12 and ring 14, and the balloon is deployed from the catheter 50 similar to the deployment of the ring and cage. Catheter 50 is also insertable remote from the placed cage and ring, wherein the catheter is advanced within a fluid passageway through the cage and ring to deploy the balloon. After placement, the balloon is filled with liquid silicone rubber through tube 52 and then detached from the needle, catheter 54 holding inflated balloon 18 in place as tube 52 is withdrawn.

Migration of cage 12 relative to ring 14 is potentially detrimental as excess travel of balloon 18 can result. Among other risks, the excess travel may reduce pumping efficiency as the response time of the valve will increase; i.e., valve 10 will take increased amounts of time to open and close. Further, if cage 12 migrates from ring 14, the balloon may become trapped while translating within the vessel. Should the balloon become trapped, it will result in an incompetent valve, thus grossly reducing the heart's pumping capacity and efficiency.

Figure 6:
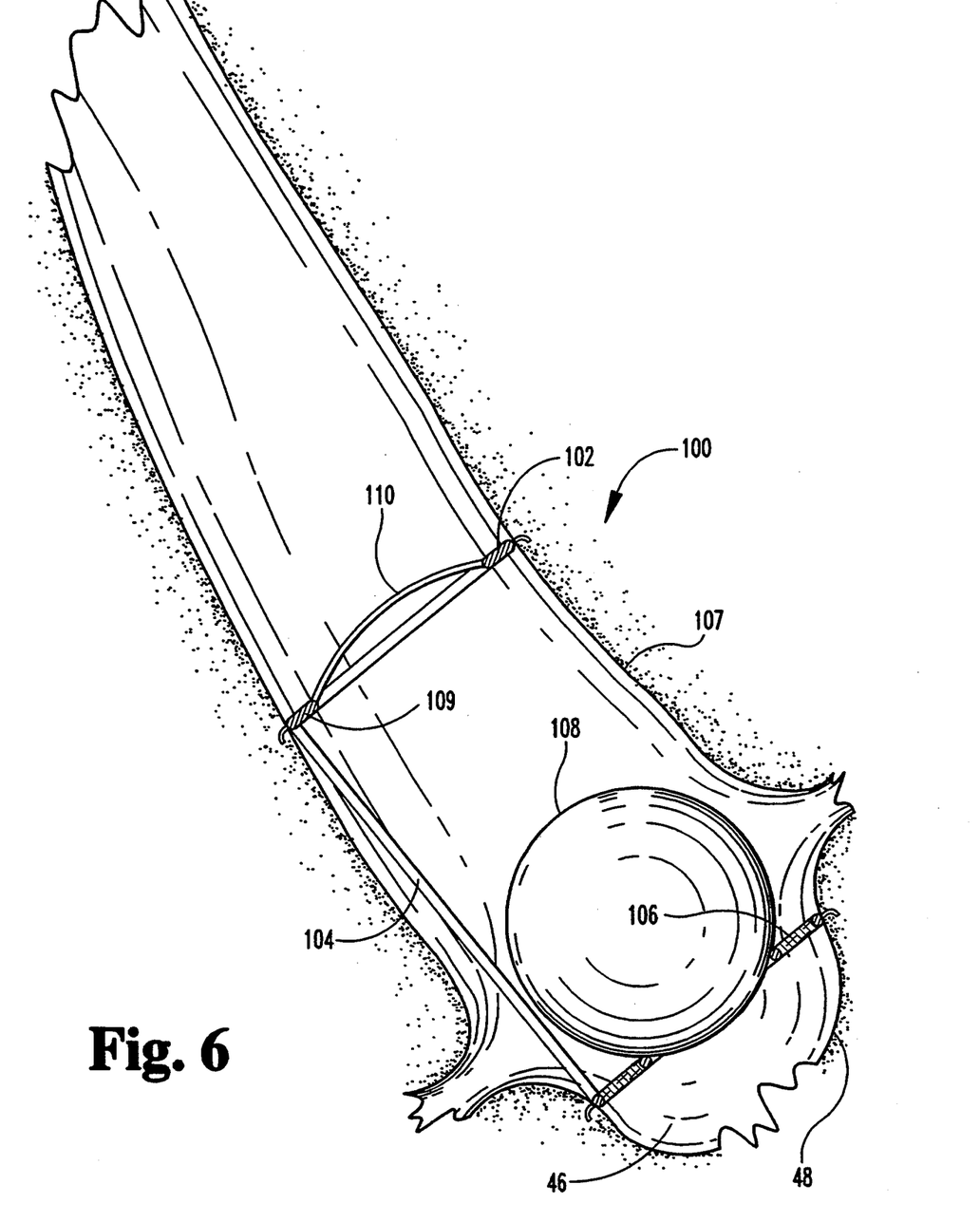
FIG. 6 is a side cross-sectional view of a prosthetic valve according to a second embodiment of the present invention.

Alternative embodiments are also envisioned which minimize these risks. Referring to FIG. 6, one such embodiment depicts a valve 100 comprising a restraining element 102 connected via tubing 104 to seat 106. Restraining element 102 comprises a ring-type spring 109 having attached across it wire segments 110 to prevent travel of poppet 108 past element 102. The opening in spring 109 is sized sufficiently large to permit fluid flow therethrough when restraining element 102 restrains poppet 108. Seat 106 is similar to ring 14 in that it provides a sealing interface for poppet 108. Rather than balloon 18 traversing substantially within a cage, as within valve 10, poppet 108 traverses within vessel 107 between element 102 and seat 106. Poppet 108 translates between a sealing position seated against seat 106 to an open position restrained from passing through element 102. Element 102 allows fluid to pass through while restraining poppet 108 in the open position.

In one specific example of the valve 10 for placement in dogs, the cage was constructed ranging from 2.5 to 3.5 cm. in diameter. The outside diameter of the ring ranged from 2.4 to 3.4 cm., varying in 2 mm. increments. After induction of general anesthesia, the right common carotid artery was surgically isolated and an 11-12 French Teflon sheath was introduced. This sheath was advanced into the ascending aorta under fluoroscopic monitoring. With the animal in the left lateral position, an aortogram was performed to determine the diameter of the sinus Valsalva and ascending aorta and to select the proper size of the prosthetic valve. Following the aortogram, the tip of the delivery sheath was positioned in the posterior non coronary cusp. A small amount of contrast material was hand-injected to check the position of the sheath and was marked by placement of a needle in the overlying skin. The prosthetic valve was then delivered through the sheath using a pusher catheter. As the ring exited the sheath, it opened and was anchored against the annulus by the barbs.

After a determination was made confirming the valve's position, the entire device was extruded into the aorta. The ring was placed below the ostia of the coronary arteries in such a way that the cusps of the aortic valve were compressed. This created a huge regurgitation and an appropriate animal model for evaluating the device. The detachable balloon was then placed into the cage. After inflation with a predetermined volume of silicone, the balloon was detached from its delivery system. The position of the ring and the competency of the valve were tested by injecting contrast media directly above the cage.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A prosthetic aortic valve assembly for percutaneous insertion and placement within a fluid passageway of a living body, comprising:
   a valve seat;
   a restraining element;
   a poppet;
   said valve assembly having a first insertion form for percutaneous insertion into the passageway, said first insertion form including a compressed valve seat, a compressed restraining element, and a compressed poppet; and
   each element of said valve assembly expanding to a second larger operational form after the assembly is placed within the passageway, said valve seat having means for sealing against the passageway and an opening for sealing engagement with said poppet, said restraining element having means for restraining passage of said poppet therethrough while permitting fluid flow therethrough, said poppet movably restrained between said valve seat and said restraining element, said poppet being movable to seal against said opening in said valve seat to prevent fluid flow therethrough and said poppet being movable to unseat from said valve seat to permit fluid flow therethrough.

2. The prosthetic valve of claim 1 further comprising means for fixedly disposing said restraining element relative to said valve seat.

3. The prosthetic valve of claim 1 wherein said seat includes a number of first barbs for attaching said valve to the passageway upon placement therein.

4. The prosthetic valve of claim 1 wherein said restraining element includes a number of second barbs for attaching said valve to the passageway upon placement therein.

5. A prosthetic aortic valve assembly for percutaneous insertion and placement within a fluid passageway of a living body, comprising:
   a valve seat;
   a restraining element;
   a poppet including an inflatable balloon, said balloon assuming the first insertion form when deflated and the second operational form when inflated;
   means for fixedly disposing said restraining element relative to said valve seat;
   said valve assembly having a first insertion form, said first insertion form including a compressed valve seat, a compressed restraining element, and a compressed poppet for percutaneous insertion into the passageway; and
   said valve assembly expanding to a second larger operational form after the assembly is placed within the passageway, said valve seat having means for sealing against the passageway and an opening for sealing engagement with said poppet, said restraining element having means for restraining passage of said poppet there through while permitting fluid flow there through, said poppet movably restrained between said valve seat and said restraining element, said poppet being movable to seal against said opening in said valve seat to prevent fluid flow there through and said poppet being movable to unseat from said valve seat to permit fluid flow therethrough.

6. The prosthetic valve of claim 5 wherein:
   said seat includes a flexible ring;
   said restraining element includes a flexible cage; and
   wherein said ring and cage are resiliently compressible for insertion into the passageway in the first insertion form and for self-expansion against the passageway to operate in the passageway in the second operational form.

7. The prosthetic valve of claim 6 wherein said cage includes a flexible self-expanding stent with flexible wire segments looped across an end of said stent and attached thereto, said cage being adapted to support said passageway in open condition and said wire segments being adapted to restrain movement of said balloon through the passageway.

8. The prosthetic valve of claim 7 wherein said flexible ring includes a number of first barbs for attaching said valve to the passageway upon placement therein.

9. The prosthetic valve of claim 8 wherein said flexible cage includes a number of second barbs for attaching said valve to said passageway upon placement therein.

10. The prosthetic valve of claim 9 wherein said stent includes a flexible wire formed into a closed zig-zag configuration, the wire including an endless series of straight sections and a plurality of bends, the straight sections joined by the bends to form the stent and the bends defining ends of said stent.

11. The prosthetic valve of claim 10 wherein said flexible ring includes:
   a first smaller diameter circular spring having a first smaller diameter opening less than the expanded diameter of the poppet;
   a concentric second larger diameter circular spring having a second larger diameter adapted to engage the passageway; and
   a flexible membrane attached between said circular springs and sealing fluid from flowing through said valve when said balloon is seated against said ring preventing fluid flow through said first smaller diameter opening.

12. The prosthetic valve of claim 11 wherein said balloon further includes a one-way valve for inflation, said valve containing fluid within said balloon after inflation.

13. The prosthetic valve of claim 12 wherein said balloon is inflated with liquid silicone rubber after placement within the passageway.

14. A prosthetic aortic valve assembly for percutaneous insertion and placement within a fluid passageway of a living body, comprising:
   a valve seat;
   a restraining element;
   a poppet including an inflatable balloon, said balloon assuming the first insertion form when deflated and the second operational form when inflated;
   said valve assembly having a first insertion form, said first insertion form including a compressed valve seat, a compressed restraining element, and a compressed poppet for percutaneous insertion into the passageway; and
   said valve assembly expanding to a second larger operational form after the assembly is placed within the passageway, said valve seat having means for sealing against the passageway and an opening for sealing engagement with said poppet, said restraining element having means for restraining passage of said poppet there through while permitting fluid flow there through, said poppet movably restrained between said valve seat and said restraining element, said poppet being movable to seal against said opening in said valve seat to prevent fluid flow there through and said poppet being movable to unseat from said valve seat to permit fluid flow therethrough.

15. The prosthetic valve of claim 14 wherein said balloon further includes a one-way valve for inflation, said valve containing fluid within said balloon after inflation.

16. The prosthetic valve of claim 15 wherein said balloon is inflated with liquid silicone rubber after placement within the passageway.

* * * * *